United States Patent
Doll et al.

(10) Patent No.: US 9,009,901 B2
(45) Date of Patent: Apr. 21, 2015

(54) ORAL CARE DEVICES HAVING AUTOMATIC MODE SELECTION

(75) Inventors: Alexander Franz Doll, Kronberg (DE); Uwe Jungnickel, Koenigstein (DE); Rene Guebler, Friedberg (DE); Niclas Altmann, Schoneck (DE)

(73) Assignee: Braun GmbH, Kronberg (DE)

( * ) Notice: Subject to any disclaimer, the term of this patent is extended or adjusted under 35 U.S.C. 154(b) by 62 days.

(21) Appl. No.: 13/492,565

(22) Filed: Jun. 8, 2012

(65) Prior Publication Data

US 2013/0071805 A1 Mar. 21, 2013

Related U.S. Application Data

(60) Provisional application No. 61/536,678, filed on Sep. 20, 2011.

(51) Int. Cl.
*A46B 15/00* (2006.01)
*A46B 13/02* (2006.01)
*A61C 17/22* (2006.01)
(Continued)

(52) U.S. Cl.
CPC *A61N 1/322* (2013.01); *A61N 1/32* (2013.01); *A46B 15/0022* (2013.01); *A61N 5/0601* (2013.01); *A61N 1/26* (2013.01); *A61N 1/306* (2013.01); *A61C 17/221* (2013.01); *A46B 15/0008* (2013.01); *A46B 15/0024* (2013.01); *A46B 15/00* (2013.01); *A61C 17/22* (2013.01);
(Continued)

(58) Field of Classification Search
USPC .............................................. 15/167.1, 22.1
See application file for complete search history.

(56) References Cited

U.S. PATENT DOCUMENTS 3,520,297 A 7/1970 Bechtold
4,969,868 A 11/1990 Wang
(Continued)

FOREIGN PATENT DOCUMENTS

CN 000002678597 Y 2/2005
CN 000101340856 A 1/2009
(Continued)

OTHER PUBLICATIONS

M.-C.D.N.J.M. Huysmansl, C. Longbottom, N.B. Pitts, P. Los, and P.G. Bruce; Impedance Spectroscopy of Teeth with and without Approximal Caries Lesionsan in vitro Study; J Dent Res 75(11): 1871-1878, Nov. 1996.
(Continued)

*Primary Examiner* — Monica Carter
*Assistant Examiner* — Stephanie Berry
(74) *Attorney, Agent, or Firm* — Vladimir Vitenberg

(57) ABSTRACT

Embodiments of the present disclosure are directed to oral care devices, system and methods for advanced ionic micro-current control. In some embodiments, an oral care device is actuated upon completion of an electric circuit by a users hand and oral cavity. The electrode on an oral care implement may be configured to lose conductivity over time to indicate a replacement oral care implement is need. In some embodiments, a controller of the oral care device may detect the type of oral care implement and control the ionic micro-current accordingly. Additionally, embodiments may detect a region within the oral cavity that the oral care device is in contact with and apply the ionic micro-current accordingly. Further, in some embodiments, the health status of various regions of a user's oral cavity may be detected and monitored over time.

16 Claims, 8 Drawing Sheets

(51) Int. Cl.
- *A61N 1/32* (2006.01)
- *A61N 5/06* (2006.01)
- *A61N 1/26* (2006.01)
- *A61N 1/30* (2006.01)
- *A61C 19/04* (2006.01)

(52) U.S. Cl.
CPC .............. *A61C 17/222* (2013.01); *A61C 19/04* (2013.01); *A46B 2200/1066* (2013.01)

(56) References Cited

U.S. PATENT DOCUMENTS

| | | | |
|---|---|---|---|
| 5,280,429 | A | 1/1994 | Withers |
| 5,706,542 | A | 1/1998 | Okada |
| 6,432,387 | B1 | 8/2002 | Kaizuk |
| 6,743,015 | B2 | 6/2004 | Magnani |
| 6,952,856 | B2 | 10/2005 | Kaizuka |
| 7,270,878 | B2 | 9/2007 | Kaizuka |
| 7,975,341 | B2 | 7/2011 | Cai et al. |
| 2002/0189041 | A1* | 12/2002 | Duff et al. ............... 15/167.1 |
| 2003/0135940 | A1 | 7/2003 | Lev |
| 2003/0163170 | A1 | 8/2003 | Faisandier |
| 2003/0233877 | A1 | 12/2003 | Grez |
| 2004/0193235 | A1 | 9/2004 | Altshuler et al. |
| 2005/0011025 | A1 | 1/2005 | Hilscher et al. |
| 2005/0266373 | A1 | 12/2005 | Lin |
| 2006/0070195 | A1 | 4/2006 | Morita |
| 2006/0270942 | A1 | 11/2006 | McAdams |
| 2006/0279896 | A1 | 12/2006 | Bruwer |
| 2007/0232983 | A1 | 10/2007 | Smith |
| 2007/0259310 | A1 | 11/2007 | Goodson et al. |
| 2008/0003540 | A1 | 1/2008 | Khawaled |
| 2008/0060148 | A1 | 3/2008 | Pinyayev et al. |
| 2008/0083074 | A1* | 4/2008 | Taniguchi et al. ............ 15/22.1 |
| 2008/0086189 | A1 | 4/2008 | Taniguchi |
| 2008/0183249 | A1* | 7/2008 | Kitagawa et al. ............... 607/79 |
| 2009/0087813 | A1 | 4/2009 | Cai et al. |
| 2009/0264792 | A1 | 10/2009 | Mazar |
| 2010/0281636 | A1 | 11/2010 | Ortins |
| 2011/0080122 | A1 | 4/2011 | Klemm et al. |
| 2011/0232014 | A1* | 9/2011 | Uchida et al. ............... 15/167.1 |
| 2012/0266397 | A1* | 10/2012 | Iwahori ............ 15/22.1 |
| 2013/0071805 | A1 | 3/2013 | Doll et al. |
| 2013/0071806 | A1 | 3/2013 | Doll et al. |
| 2013/0071807 | A1 | 3/2013 | Doll et al. |
| 2013/0072851 | A1 | 3/2013 | Doll et al. |

FOREIGN PATENT DOCUMENTS

| | | | |
|---|---|---|---|
| DE | 196 05 845 | A1 | 8/1997 |
| DE | 000010244575 | B3 | 5/2004 |
| DE | 000004012413 | A1 | 12/2005 |
| DE | 10159395 | | 12/2005 |
| DE | 10200402263 | | 12/2005 |
| DE | 102004029684 | | 12/2005 |
| DE | 102005007919 | A1 | 8/2006 |
| EP | 1935371 | A1 | 6/2008 |
| EP | 000001980375 | A1 | 10/2008 |
| EP | 2 522 303 | A1 | 11/2012 |
| GB | 000002030855 | A | 1/1959 |
| GB | 2317555 | A | 4/1998 |
| GB | 2414658 | A | 12/2005 |
| JP | 61-048356 | A | 10/1986 |
| JP | 63-300710 | A | 12/1988 |
| JP | 21-59208 | A | 6/1990 |
| JP | 22-24615 | A | 9/1990 |
| JP | 22-77407 | A | 11/1990 |
| JP | 22-83311 | A | 11/1990 |
| JP | 23-09908 | A | 12/1990 |
| JP | 42-15706 | A | 8/1992 |
| JP | 53-05010 | A | 11/1993 |
| JP | 61-81996 | A | 7/1994 |
| JP | 80-80219 | A | 3/1996 |
| JP | 000008275961 | A | 10/1996 |
| JP | 90-0351 | A | 1/1997 |
| JP | 90-65931 | A | 3/1997 |
| JP | 91-40453 | A | 6/1997 |
| JP | 91-91936 | A | 7/1997 |
| JP | 92-66818 | A | 10/1997 |
| JP | 10042962 | A | 2/1998 |
| JP | 10-127346 | A | 5/1998 |
| JP | 2001-309820 | | 11/2001 |
| JP | 2003164334 | A | 6/2003 |
| JP | 2004041684 | A | 2/2004 |
| JP | 2004321765 | A | 11/2004 |
| JP | 002010213908 | A | 9/2010 |
| KR | 102003084978 | A | 11/2003 |
| KR | 1020080054353 | | 6/2008 |
| WO | WO9636393 | A1 | 11/1996 |
| WO | WO02071971 | | 9/2002 |
| WO | WO02071972 | A1 | 9/2002 |
| WO | WO2004001948 | | 12/2003 |
| WO | WO2005062710 | A2 | 7/2005 |
| WO | WO2006043758 | A1 | 4/2006 |
| WO | WO2006046543 | A1 | 5/2006 |
| WO | WO2006087927 | A1 | 8/2006 |
| WO | WO2006104463 | A1 | 10/2006 |
| WO | WO2007047568 | A1 | 4/2007 |
| WO | WO2007072430 | A3 | 6/2007 |
| WO | WO2010106850 | A1 | 9/2010 |
| WO | WO2011013533 | A1 | 2/2011 |
| WO | WO2011/077299 | * | 6/2011 ............ A46B 15/00 |
| WO | WO 2011/077299 | A1 | 6/2011 |
| WO | WO2011/077299 | A1 | 6/2011 |
| WO | WO 2011077299 | * | 6/2011 ............ A46B 15/00 |
| WO | WO2011/077299 | * | 6/2011 ............ A46B 15/02 |
| WO | WO2011083793 | A1 | 7/2011 |

OTHER PUBLICATIONS

International Search Report for PCT/US2012/056176, dated Dec. 10, 2012.

International Search Report for PCT/US2012/056175, dated Dec. 14, 2012.

International Search Report for PCT/US2012/056177, dated Dec. 18, 2012.

International Search Report for PCT/US2012/055279, dated Dec. 14, 2012.

U.S. Appl. No. 13/492,582, filed Jun. 8, 2012, Alexander Franz Doll.et al.

U.S. Appl. No. 13/492,595, filed Jun. 8, 2012, Alexander Franz Doll et al.

U.S. Appl. No. 61/536,678, filed Sep. 20, 2011, Alexander Franz Doll.

* cited by examiner

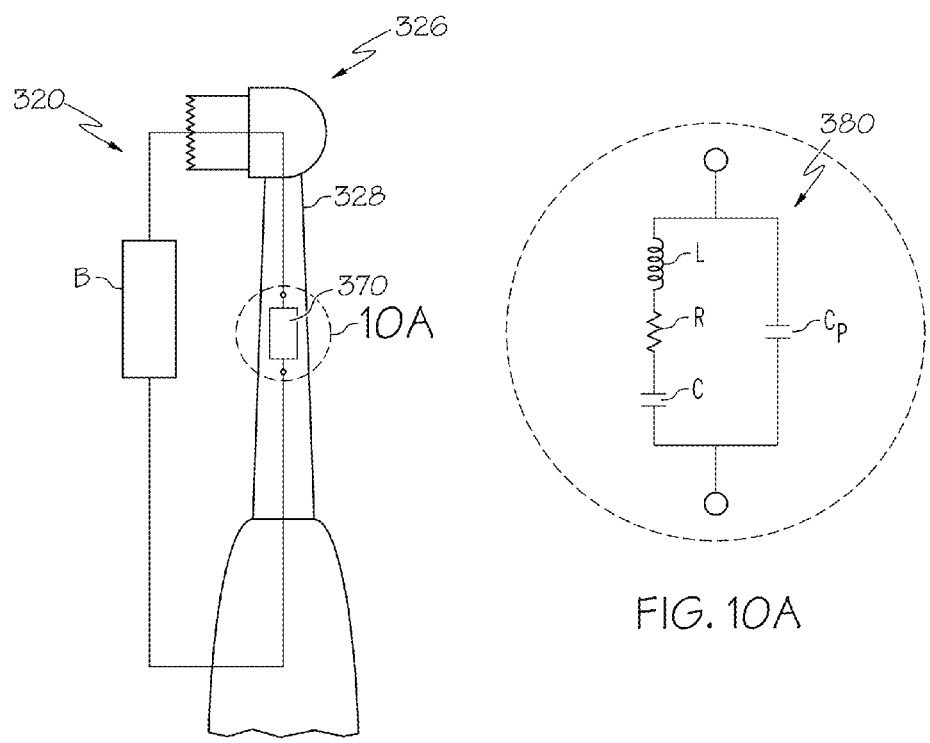
FIG. 10
FIG. 10A
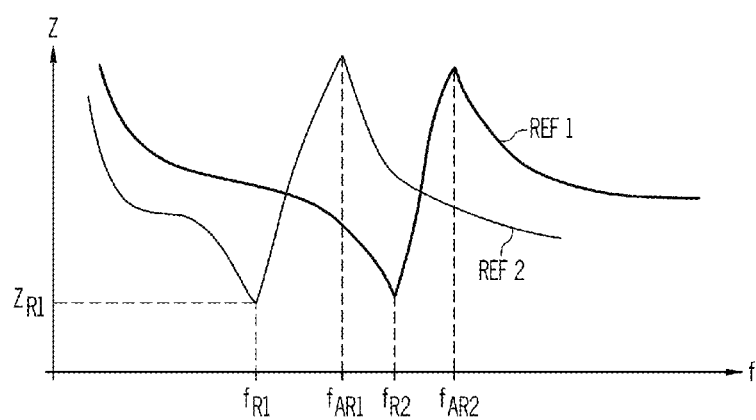
FIG. 11

ORAL CARE DEVICES HAVING AUTOMATIC MODE SELECTION

CROSS REFERENCE TO RELATED APPLICATIONS

This application claims the benefit of U.S. Provisional Application Ser. No. 61/536,678 filed on Sep. 20, 2011.

TECHNICAL FIELD

The present application relates generally to oral care devices and, more specifically, oral care devices capable of providing ionic micro-currents to the oral cavity of a user for iontophoresis applications.

SUMMARY

Iontophoresis is a medical technique that utilizes a small current (or charge) to deliver medicine or chemicals through the skin of a patient. Iontophoresis applications are numerous and may be used to treat many afflictions such as arthritis, warts, herpes and many others. Recently, iontophoresis is being used in oral care devices such as tooth brushes to aid in removing plaque from the teeth of users, as well as increase the delivery of fluorine negative ions to the teeth.

In one embodiment, an oral care device includes a handle portion and an oral care implement coupled to the handle portion. The oral care implement includes a brush head portion having brush filaments, and the oral care device further includes a first electrode located in the brush head portion and operable to be in electrical contact with an oral cavity of the user, a second electrode located in the handle portion and operable to be in electrical contact with a hand of a user, a power source providing a voltage potential between the first electrode and the second electrode, and a controller circuit electrically coupled to the first electrode, the second electrode, and the power source. Electrical contact of the second electrode at the hand of the user and electrical contact of the first electrode at the oral cavity of the user completes an electrical circuit between the first electrode and the second electrode. The first electrode is configured to be electrically decoupled from the controller circuit and the power source after a predetermined operational duration of the oral care device. The controller circuit detects a completion or an opening of the electrical circuit by measuring an impedance through the user between the hand of the user and the oral cavity of the user, such that a measured impedance above a threshold indicates the opening of the electrical circuit and a measured impedance below the threshold indicates the completion of the electrical circuit. Upon detection of the completion of the electrical circuit, the controller circuit controls the oral care device to operate at a first operational mode, and, upon detection of the opening of the electrical circuit, the controller circuit controls the oral care device to operate at a second operational mode.

In another embodiment, an oral care device includes a handle portion and an oral care implement coupled to the handle portion, wherein the oral care implement includes a brush head portion having brush filaments. The oral care device further includes a first electrode located in the brush head portion and operable to be in electrical contact with an oral cavity of the user, a second electrode located in the handle portion and operable to be in electrical contact with a hand of a user, a power source providing a voltage potential between the first electrode and the second electrode, a vibrating actuator operable to vibrate at a vibration amplitude and frequency to translate the brush head portion at the vibration amplitude and frequency, and a controller circuit in electrical communication with the vibrating actuator, the first electrode, the second electrode, and the power source. Electrical contact of the second electrode at the hand of the user and electrical contact of the first electrode at the oral cavity of the user completes an electrical circuit between the first electrode and the second electrode. The controller circuit detects a completion or an opening of the electrical circuit by measuring an impedance through the user between the hand of the user and the oral cavity of the user, such that a measured impedance above a threshold indicates the opening of the electrical circuit and a measured impedance below the threshold indicates the completion of the electrical circuit. Upon detection of the completion of the electrical circuit, the controller circuit controls the oral care device to operate in the first operational mode by generating a micro-current I through the user between the first electrode and the second electrode, and controlling the vibrating actuator to vibrate at the operational vibration amplitude and frequency. Upon detection of the opening of the electrical circuit, the controller circuit controls the oral care device to operate in the second operational mode by stopping the micro-current I through the user between the first electrode and the second electrode, and controlling the vibrating actuator to stop vibrating at the operational vibration amplitude and frequency.

In yet another embodiment, an oral care device includes a handle portion, and an oral care implement coupled to the handle portion, wherein the oral care implement includes a brush head portion having brush filaments. The oral care device further includes a first electrode located in the brush head portion and operable to be in electrical contact with an oral cavity of a user, a second electrode located in the handle portion and operable to be in electrical contact with a hand of the user, a power source providing a voltage potential between the first electrode and the second electrode, and a controller circuit in electrical communication with the first electrode, the second electrode, and the power source. Electrical contact of the second electrode at the hand of the user and electrical contact of the first electrode at the oral cavity of the user completes an electrical circuit between the first electrode and the second electrode. The controller circuit controls a micro-current I that passes through the user between the first electrode and the second electrode, and determines an impedance of the electrical circuit based on the micro-current I. The controller circuit controls the oral care device to operate in a first operational mode when the impedance is within a first impedance range, and controls the oral care device to operate in a second operational mode when the impedance is within a second impedance range.

In yet another embodiment, an oral care device includes a handle portion, and an oral care implement coupled to the handle portion, wherein the oral care implement includes a brush head portion having brush filaments. The oral care device further includes a first electrode located in the brush head portion and operable to be in electrical contact with a location within an oral cavity of a user, a second electrode located in the handle portion and operable to be in electrical contact with a hand of the user, a power source providing a voltage potential between the first electrode and the second electrode, and a controller circuit in electrical communication with the first electrode, the second electrode, and the power source. Electrical contact of the second electrode at the hand of the user and electrical contact of the first electrode at the location within the oral cavity of the user completes an electrical circuit between the first electrode and the second electrode. Upon a completion of the electrical circuit, the controller circuit generates a micro-current I through the user between the first electrode and the second electrode such that the micro-current I enhances delivery of chemical actives to the location within the oral cavity of the user, the chemical actives present in an oral care substance located within the oral cavity of the user. The controller circuit calculates an amount of chemical actives delivered to the location within the oral cavity of the user at a time t based at least in part on a value of the micro-current I through the user, the oral care substance, and a polarity of the second electrode with respect to the first electrode.

In yet another embodiment, an oral care device includes a handle portion, and an oral care implement coupled to the handle portion, wherein the oral care implement includes a brush head portion having brush filaments. The oral care device further includes a first electrode located in the brush head portion and operable to be in electrical contact with a hard tissue within an oral cavity of a user, a second electrode located in the handle portion and operable to be in electrical contact with a hand of the user, a power source providing a voltage potential between the first electrode and the second electrode, and a controller circuit in electrical communication with the first electrode, the second electrode, and the power source. Electrical contact of the second electrode with the hand of the user and electrical contact of the first electrode with the hard tissue within the oral cavity of the user completes an electrical circuit between the first electrode and the second electrode. Upon a completion of the electrical circuit, the controller circuit generates a substantially sinusoidal micro-current I through the user between the hand of the user and the hard tissue within the oral cavity of the user at a frequency that varies across a frequency range. The controller circuit measures a fundamental-harmonic component of a response of the substantially sinusoidal micro-current I through the electric circuit, and calculates a system impedance based at least in part on the fundamental-harmonic component. The controller circuit compares the system impedance with a plurality of impedance values corresponding to a plurality of health statuses corresponding to one or more teeth, selects a closest impedance value to the system impedance, and stores a selected health status corresponding to the closest impedance value.

In yet another embodiment, a method of hard tissue diagnosis using an electric toothbrush having an oral cavity electrode and a gripping electrode includes generating a substantially sinusoidal micro-current I through an electric circuit closed by a user of the electric toothbrush by contact of the oral cavity electrode with a hard tissue within an oral cavity of the user and by contact of the gripping electrode with a hand of the user, wherein the substantially sinusoidal micro-current I passes through at least the hard tissue within the oral cavity of the user at a frequency that varies across a frequency range. The method further includes detecting a response of the substantially sinusoidal micro-current I through the electric circuit at the gripping electrode, measuring a fundamental-harmonic component of the response, and calculating a system impedance based at least in part on the fundamental-harmonic component. The method further includes comparing the system impedance with a plurality of impedance values corresponding to a plurality of health statuses, selecting a closest impedance value to the system impedance, and storing a selected health status corresponding to the closest impedance value.

In yet another embodiment, an oral care device includes a handle portion, and an oral care implement coupled to the handle portion, wherein the oral care implement includes a brush head portion having brush filaments. The oral care device further includes a first electrode located in the brush head portion and operable to be in electrical contact with an oral cavity of a user, a second electrode located in the handle portion and operable to be in electrical contact with a hand of the user, an impedance element having an impedance characteristic within the oral care implement and electrically coupled to the first electrode, a power source providing a voltage potential between the first electrode and the second electrode, and a controller circuit in electrical communication with the first electrode, the second electrode, the impedance element, and the power source. Electrical contact of the second electrode at the hand of the user and electrical contact of the first electrode at the oral cavity of the user completes an electrical circuit between the first electrode and the second electrode. The controller circuit determines an impedance of the oral care implement, wherein the impedance element of the oral care implement affects the determined impedance. Additionally, the controller circuit generates a micro-current I through the user between the first electrode and the second electrode at a first micro-current amplitude when the impedance is within a first impedance range, and generates the micro-current I through the user between the first electrode and the second electrode at a second micro-current amplitude when the impedance is within a second impedance range.

In yet another embodiment, an oral care device includes a handle portion, and an oral care implement coupled to the handle portion, wherein the oral care implement includes a brush head portion having brush filaments. the oral care device further includes a first electrode located in the brush head portion and operable to be in electrical contact with an oral cavity of the user, and a second electrode located in the handle portion and operable to be in electrical contact with a hand of a user, wherein electrical contact of the second electrode at the hand of the user and electrical contact of the first electrode at the oral cavity of the user completes an electrical circuit between the first electrode and the second electrode. The oral care device further includes a power source providing a voltage potential between the first electrode and the second electrode, and a controller circuit in electrical communication with the first electrode, the second electrode, and the power source. The controller circuit generates an evaluation micro-current $I_{eval}$ through the electrical circuit, wherein the evaluation micro-current $I_{eval}$ sweeps across an evaluation frequency range, and detects a resonant electrical frequency of the oral care implement based on a frequency response of the oral care implement in response to the evaluation micro-current across the evaluation frequency range. The controller circuit further generates a micro-current I through the user between the first electrode and the second electrode at a first micro-current amplitude when the detected resonant electrical frequency is within a first frequency range, and generates the micro-current I through the user between the first electrode and the second electrode at a second micro-current amplitude when the detected resonant electrical frequency is within a second frequency range.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate various embodiments described herein, and together with the description serve to explain the principles and operations of the claimed subject matter.

FIGS. 10 and 10A schematically depicts an oral care implement comprising an electro-active polymer according to one or more embodiments illustrated and described herein; and FIG. 11 graphically depicts an impedance response as a function of frequency for two oral care implement refills according to one or more embodiments illustrated and described herein.

DETAILED DESCRIPTION OF THE INVENTION

Embodiments disclosed herein are generally related to oral care devices, such as electric toothbrushes, that provide ionic micro-currents to an oral cavity of a user to deliver chemical actives by iontophoresis. More specifically, embodiments are directed to oral care devices capable of detecting when the oral care device is grasped by a user and positioned within the user's mouth, detecting a region of an oral cavity of the user and changing a brushing mode accordingly, detecting a type of oral care implement coupled to the oral care device and changing a brushing mode accordingly, and diagnosing the health status of teeth.

Embodiments may be implemented in a device having a first electrode that is held by the user or is otherwise in electrical contact with some region of the user's body, and a second electrode that is to be applied at the region of iontophoretic interest (e.g., the oral cavity of a user). Micro-current flows through the user's body between the regions of the body that are in contact with the first and second electrodes because the user's body completes an electric circuit between the first and second electrodes.

Figure 1:
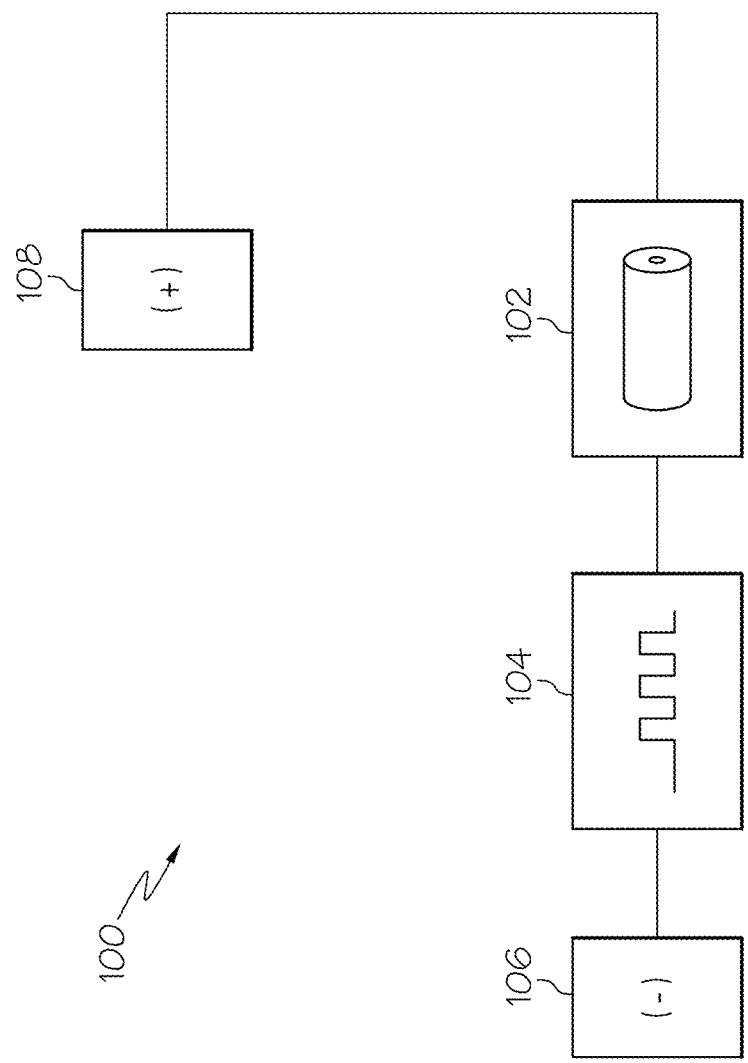
FIG. 1 schematically depicts electrical components of an oral care device according to one or more embodiments illustrated and described herein.

Referring now to FIG. 1, a general schematic of some of the components of one embodiment of an oral care device 100 is illustrated. The oral care device 100 generally comprises a power source 102, a controller circuit 104, a first electrode 106 and a second electrode 108. The power source 102 may be any power source capable of producing micro-currents (ionic) according to the particular application in which the oral care device 100 is implemented. As an example and not a limitation, the power source 102 may comprise a battery capable of providing micro-currents in the range of 50 to 1000 µA. The power source 102 may also be an AC-DC converter circuit, DC-DC voltage regulator circuit, or any appropriate circuit to obtain the voltage levels and micro-current levels particular to the iontophoresis application. As an example and not a limitation, the power source 102 may produce a voltage potential of about 30 volts to increase the iontophoresis effect and overcome the high electrical resistance of the human body portion of the electrical (ionic) circuit.

The first and second electrodes 106, 108 are electrodes that are configured to be in electrical contact with a user's body. Accordingly, the first and second electrodes 106, 108 should be electrically conductive. In one embodiment, the first and second electrodes 106, 108 are made of a metallic material. In another embodiment, the first and/or second electrode 106, 108 may be a touch electrode comprising a non-metal material filled with carbon filling as described in U.S. patent application Ser. No. 12/014,487 entitled "Oral Care Device" (e.g., carbon fibers that are dispersed in a non-electrically conductive resin). It is noted that although the first electrode is illustrated as being associated with a negative polarity (−) and the second electrode is illustrated as being associated with a positive polarity (+), embodiments are not limited thereto. The first electrode may be associated with a positive polarity and the second electrode may be associated with a negative polarity.

Figure 5:
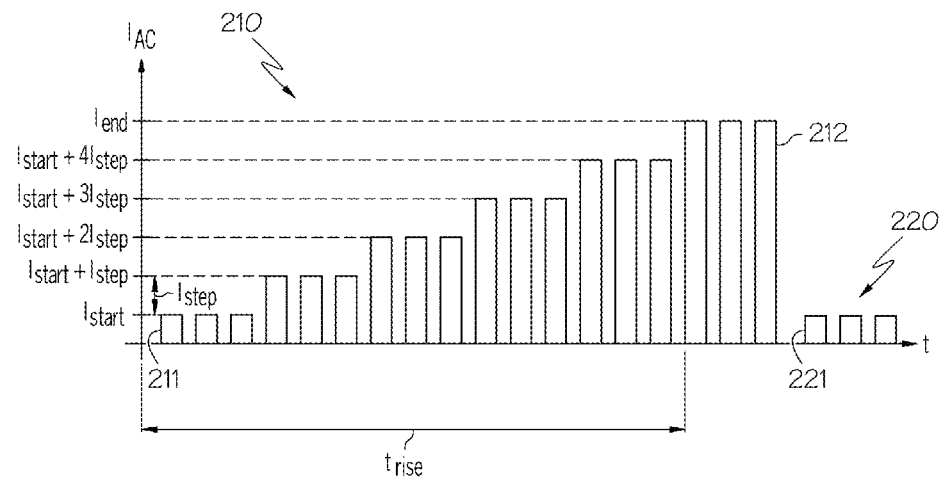
FIG. 5 graphically depicts an alternating current ramping micro-current method according to one or more embodiments illustrated and described herein.

The controller circuit 104 is a circuit that is capable of providing ionic current upon completion of an electrical circuit through the body of a user at the desired micro-current levels. Further, the controller circuit 104 effectuates the ramping control of micro-current that is applied to the user to limit the sensation that is experienced by the user. As an example and not a limitation, FIG. 5 depicts an exemplary micro-current control waveform that may be produced by the current control circuit 104. These micro-current control methods, as well as the current control circuit 104, will be described in greater detail below.

Figure 2:
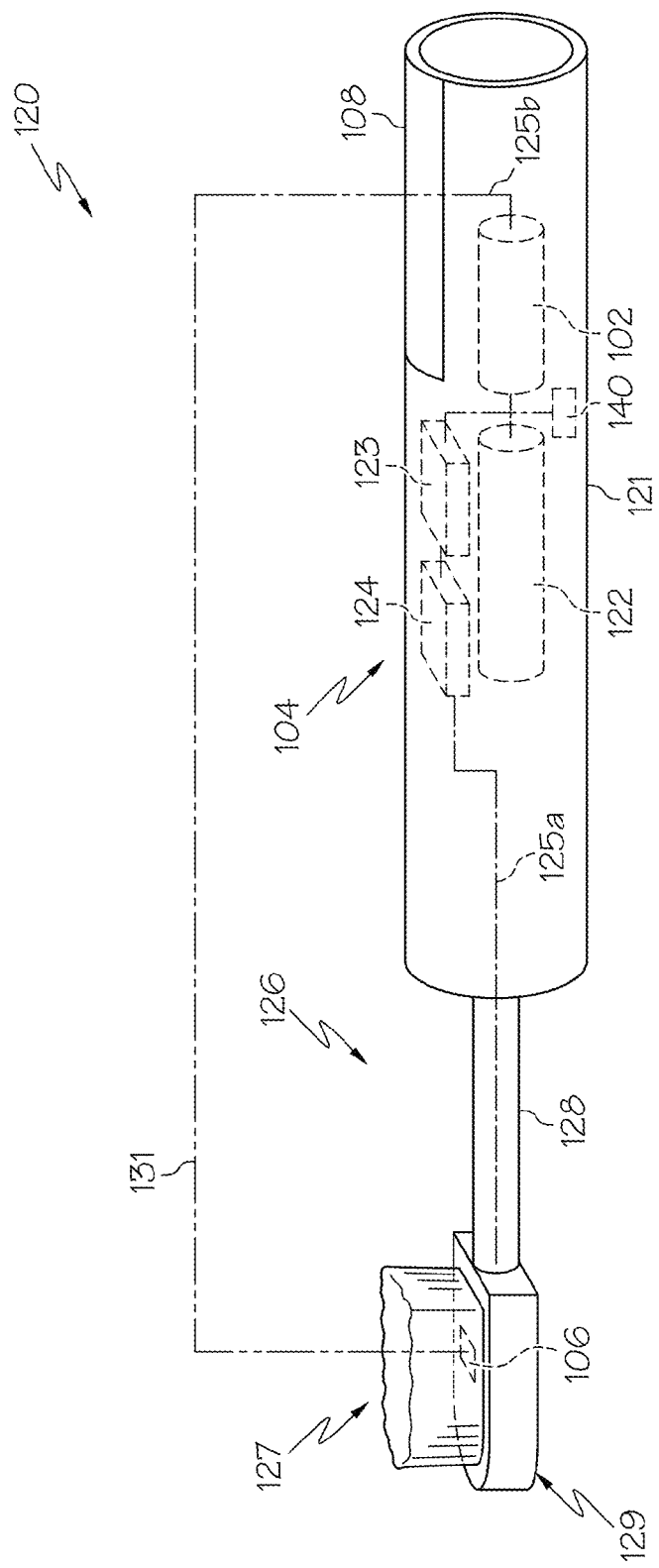
FIG. 2 schematically depicts an oral care device according to one or more embodiments illustrated and described herein.

FIG. 2 depicts a graphical illustration of an oral care device 120 according to one or more embodiments. It should be understood that the arrangement of the components of the oral care device 120 is for illustrative purposes only and embodiments are not limited to such arrangement of components or configurations of the illustrated oral care device 120. The illustrated oral care device 120 comprises a body housing and an oral care implement 126. The body housing defines a handle portion 121 on a first end of the oral care device 120. The oral care implement 126 is coupled to the handle portion 121 defining a second end of the oral care device 120. In one embodiment, the oral care implement 126 is removably coupled to the handle portion 121 such that oral care implements of differing configurations may be attached to the handle portion 121 (e.g., a tongue cleanser or a flossing implement). In an alternative embodiment, the oral care implement 126 is not removable from the handle portion 121 such that the handle portion 121 and the oral care implement 126 are one integral component. The handle portion 121 may be made of non-electrically conductive material, such as molded plastic, for example.

The illustrated oral care implement 126 generally comprises a stem portion 128 and a brush head portion 129 that is configured as an electric toothbrush head having toothbrush bristles 127 associated therewith. Both the stem portion 128 and the brush head portion 129 may be made of a non-electrically conductive material, such as a plastic material. The oral care implement 126 has a first electrode 106 that may comprise one or more electrically conductive regions. In the illustrated embodiment, the first electrode 106 comprises an electrically conductive pad that is located within an opening of the brush head portion 129 such that the electrically conductive pad of the first electrode 106 is exposed to the oral cavity of a user during operation of the oral care device 120.

As illustrated in FIG. 2, the second electrode 108 is provided in the handle portion 121 such that it may be in electrical contact with the hand of a user when the user grips the handle portion 121 to operate the oral care device 120. As described above, the second electrode 108 may be made of metallic material, a non-conductive resin with conductive carbon fibers dispersed therein, or any other electrically conductive material. It should be understood that embodiments are not limited to the configuration of the second electrode illustrated in FIG. 2. In one embodiment, an optional vibrating actuator 122 is provided and coupled to the power source 102. The vibrating actuator 122 may be configured to oscillate at a high frequency to provide vibration to the oral care device 120. The handle portion 121 may also comprise other components, such as ON/OFF buttons or switches 162 (see FIG. 8), mode selection buttons or switches, etc.

Maintained within the handle portion 121 are various electrical components that produce the therapeutic ionic microcurrents. The power source 102 (i.e., a battery) is positioned within the housing with a first polarity (e.g., a positive polarity) of the power source 102 electrically coupled to the second electrode 108. The opposite polarity (e.g., a negative polarity) of the power source 102 is electrically associated with the first electrode 106 in the oral care implement 126 through the controller circuit 104. The polarity associated with the first and second electrodes 106, 108 may be reversed depending on the particular application.

The controller circuit 104 may be mounted on a printed circuit board or other structure within the handle portion 121. As shown in FIG. 2, the controller circuit 104 may comprise a pulse generation circuit 123 and a pulse drive circuit 124. The pulse generation circuit 123 and pulse drive circuit 124 are illustrated at two physically separate circuits but it should be understood that the two circuits may be implemented in a single circuit (or integrated circuit) in some embodiments. The pulse generation circuit 123 may generate the waveforms that are desired to be applied to the user, and the pulse drive circuit 124 may amplify the waveforms to have the appropriate current values for the particular iontophoresis application. An exemplary waveform is depicted in FIG. 5.

An electric (ionic) circuit is provided by the electrical connection between the negative polarity of the power source 102 and the controller circuit 104, the controller circuit 104 and first electrode 106 (depicted by dashed line 125a), the positive polarity of the power source 102 and the second electrode 108 (depicted by dashed line 125b), and the conductive path between a hand and the oral cavity of the user (depicted by dashed line 131). The circuit is made when the user grips the first electrode 106 of the oral care device 120 and places the brush head portion 129 and first electrode 106 in his or her mouth. The circuit is opened when the user removes the brush head portion 129 and the first electrode 106 from his or her mouth. More generally, the circuit is made when a user grips a second electrode 108 of an oral care device 100 and applies the first electrode 106 of the oral care device 100 to his or her oral cavity.

In some embodiments, the oral care device 100 may also comprise a wireless communications module 140 for transmitting data both to and from the oral care device 100. The wireless communications module 140 may be configured to wirelessly communicate to external components, such as a mobile device, a computer, an external user interface (see FIG. 7), and the like. Data may include, but is not limited to, tooth diagnosis information, brushing force, brushing duration, and chemical active delivery.

Figure 3:
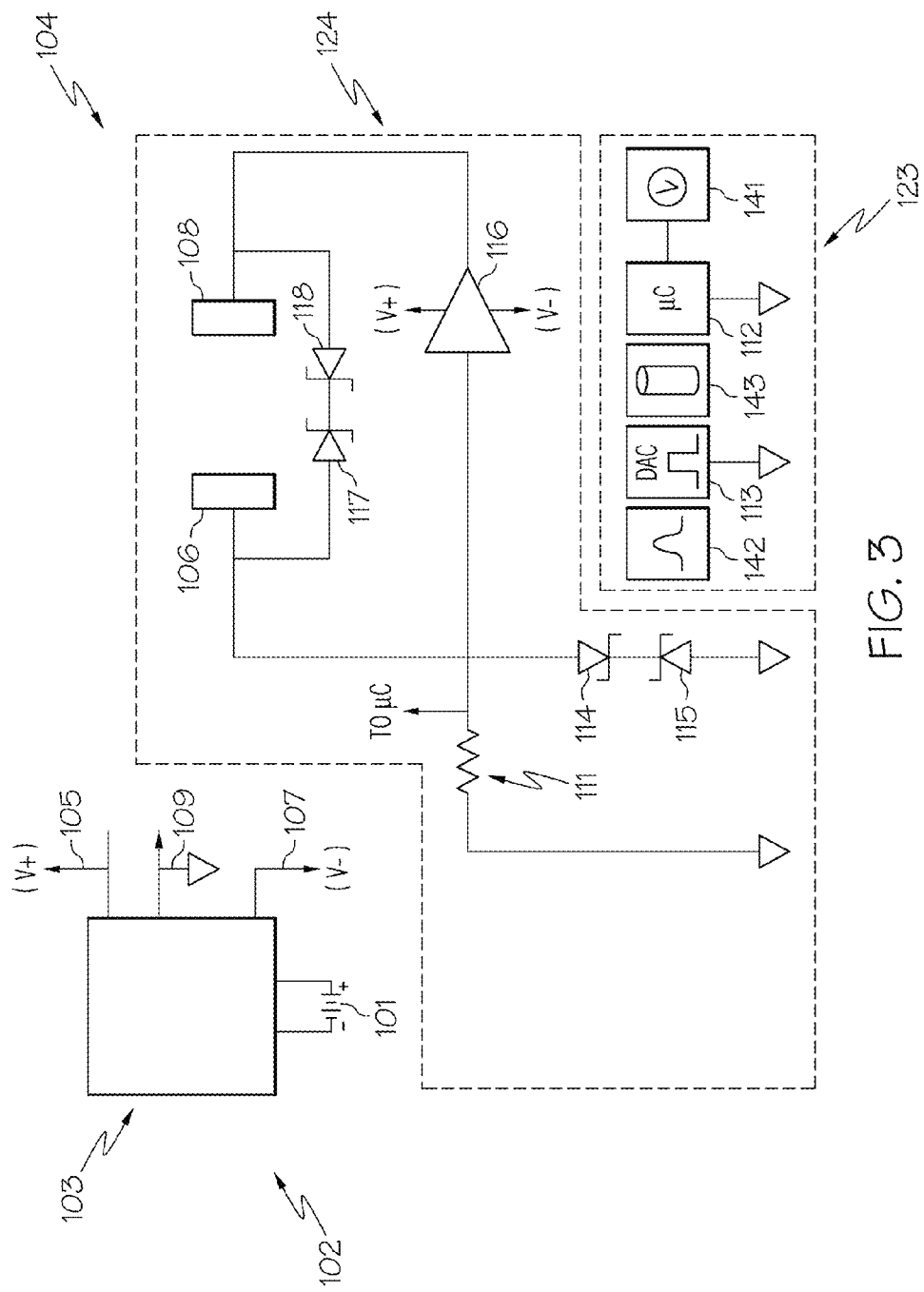
FIG. 3 schematically depicts a power source circuit and a controller circuit according to one or more embodiments illustrated and described herein.

Referring now to FIG. 3, a schematic of the controller circuit 104 and the power source 102 according to one embodiment is depicted. It should be understood that other circuits or modifications to the circuits illustrated in FIG. 3 may be used, and embodiments are not limited to the schematics of FIG. 3. The power source 102 of the illustrated embodiment comprises a battery 101 and a voltage regulator 103. In another embodiment, a voltage regulator is not provided. The voltage regulator 103 receives the voltage of the battery 101 and provides a ground reference potential 109, a positive power rail potential 105 (V+) with respect to the ground reference potential (e.g., +30V), and a negative power rail 107 (V−) with respect to the ground reference potential (e.g., −30V). It should be understood that other voltage potentials may be utilized. The positive power rail potential 105 and the negative power rail potential 107 are provided to apply anodic or cathodic polarities. The voltages provided by the voltage regulator 103 may vary depending on the particular application.

The controller circuit 104 generally comprises a pulse generation circuit 123 and a pulse drive circuit 124. The controller circuit 104 may be any circuit that is capable of producing the desired ionic current waveform (e.g., the waveform illustrated in FIG. 5) at the particular frequencies, duty cycles, current levels, etc. It should be understood that one or more of the components of the controller circuit 104 may be provided in one or more integrated circuits (e.g., an application-specific integrated circuit).

In one embodiment, the pulse generation circuit 123 comprises a microcontroller 112 and a digital-to-analog converter circuit or chip 113 (DAC) that cooperate to create a waveform that corresponds to the micro-current that is to be applied to the user. In some embodiments, the pulser generation circuit does not include a DAC. The waveforms produced by the pulse generation circuit 123 are amplified by the pulse drive circuit 124 and therefore may have voltages that are less than that necessary to produce the desired micro-currents. For example, the voltages of the waveform pulses may be in a range between zero and a logic voltage level of the microcontroller. The microcontroller 112 may provide instructions to the digital-to-analog converter 113 to produce the pulses that make up the waveforms. The waveforms may be produced in a manner other than the illustrated pulse generation circuit 123.

As stated above, the pulse drive circuit 124 is configured to amplify the waveforms provided by the pulse generation circuit 123 such that the desired micro-current levels (as well as desired frequencies and duty cycles) are applied to the user. The exemplary pulse drive circuit 124 comprises an operational amplifier 116 that receives the pulse train of the waveforms provided by the pulse generation circuit 123 as input and produces the micro-currents as output. Accordingly, the operational amplifier 116 is used as a current source that amplifies the pulse trains of the waveforms. The operational amplifier 116 is electrically connected to the positive and negative power rails of the power source 102, and is electrically coupled to a current-sensing resistor 111 that is further coupled to the ground reference potential. The output of the operational amplifier 116 is electrically coupled to the first electrode 106, which, in the context of an oral care device, is to be positioned within the oral cavity of a user. The second electrode 108 is electrically coupled to the ground reference potential through the current-sensing resistor.

The current-sensing resistor 111 is provided to provide feedback of the ionic micro-current that is passed through the user to the microcontroller 112 to monitor and make adjustments to the micro-current levels provided to the user. In one embodiment, the current-sensing resistor 111 is a 1 kΩ resistor such that 1 mV across the current-sensing resistor 111 corresponds to 1 μA.

In the embodiment illustrated in FIG. 3, the pulse generation circuit 123 and pulse drive circuit 124 may be protected by over-voltage protection devices. Zener diodes 117 and 118 clamp the voltage across the user to less than a user over-voltage value, such as 30V, for example. Zener diodes 114 and 115 protect the digital-to-analog converter 113 and microcontroller 112 by clamping the voltage to less than a pulse generation circuit over-voltage, such as 10V, for example.

In the oral care context, it is predicted that the administration of ionic current may be used to aid in the removal of plaque, as well as preventing plaque regrowth from the teeth and gums as well as administer fluorine ions to the teeth via iontophoresis. The ionic micro-current provided by the oral care device 100 may flow from the brush head portion 129, across the saliva by the user to the mouth mucosa and/or teeth, across the body into the hand of the user, and back into the handle of the oral care device 100.

Figure 4A:
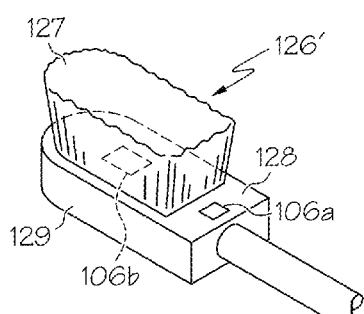
FIGS. 4A-4D schematically depict oral care implements of an oral care device according to various embodiments illustrated and described herein.
Figure 4B:
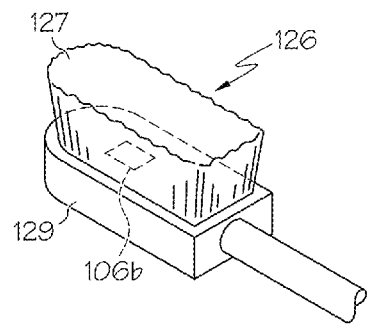
Figure 4C:
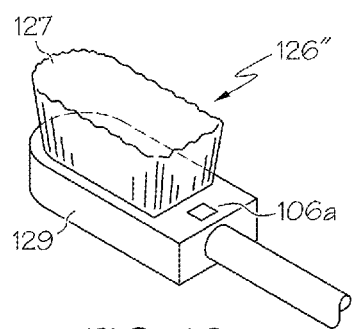

FIGS. 4A-4F illustrate various embodiments of oral care implements and first electrodes 106. The oral care implements and first electrode may take on a wide variety of configurations. It should be understood that embodiments are not limited to those configurations depicted in FIGS. 4A-4F. Referring to FIG. 4A, a brush head 126' is depicted having a first electrode that comprises a first conductive pad 106a that is positioned adjacent to the toothbrush bristles 127, and a second conductive pad 106b that is positioned under the toothbrush bristles 127. The brush head 126' depicted in FIG. 4A therefore provides two locations through which ionic current may flow. The brush head portion 129 depicted in FIG. 4B has a single conductive pad 106 positioned under the toothbrush bristles 127, while the brush head 126" depicted in FIG. 4C has a single conductive pad 106a positioned adjacent to the toothbrush bristles 127. It is also contemplated that the toothbrush bristles 127 themselves may be electrically conductive and act as the first electrode.

Figure 4D:
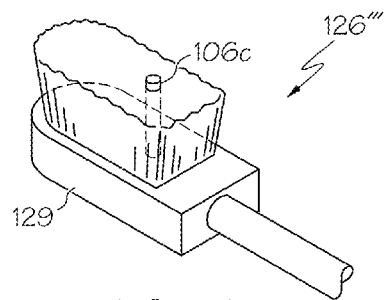
Figure 4E:
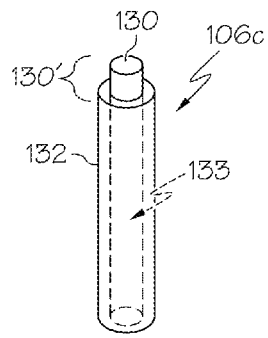
FIGS. 4E-4G schematically depict electrically conductive filaments according to various embodiments illustrated and described herein.

FIGS. 4D and 4E illustrate an embodiment in which the first electrode is in the form of one or more insulated conductor wires 106c positioned amongst the toothbrush bristles 127. FIG. 4E illustrates a close-up view of one embodiment of an insulated conductor wire 106c shown in FIG. 4D. The insulated conductor wire 106c comprises an electrically conductive wire core 130 that is made out of any electrically conductive material, such as a pliable metallic material, and an outer insulator jacket 132 that surrounds the electrically conductive wire core 130. The outer insulator jacket 132 is made of a non-conductive material that is sufficiently pliable to be used in a tooth brush application. An exposed portion 130' of the electrically conductive wire core 130 extends beyond the outer insulator jacket 132 such that it is exposed to the oral cavity of the user and may act as the first electrode as described above.

Figure 4F:
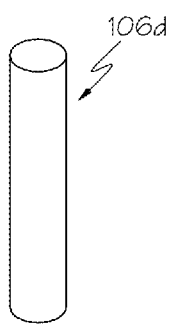

FIG. 4F illustrates an electrically conductive brush filament 106d configured as an electrically conductive material within a polymer. As an example and not a limitation, the electrically conductive brush filament 106d may comprise a polymer having electrically conductive particles (e.g., electrically conductive carbon particles, nano-particles, conductive soot) embedded therein. In another embodiment, brush filament may be coated with a conductive film or material that loses conductivity over time. For example, the colored film that is applied by a ringdye process to provide a visual indication to the users as to the wear of the bristles may be made electrically conductive.

The oral care implement may include one or more electrically conductive brush filaments 106d as the first electrode. As described in more detail below, the electrically conductive brush filament 106d depicted in FIG. 4F may be designed to lose conductivity over a period of use. For example, the electrically conductive particles may separate from the brush filament(s) over time, thereby increasing the resistivity of the electrically conductive brush filament 106d.

Ramping of Ionic Micro-current

In one embodiment, the oral cavity of the user (teeth) is under positive voltage due to the positive first electrode 106, and the second electrode 108 of the brush head portion 129 is under negative voltage to direct flow of fluorine negative ions toward the positively charged teeth.

Laboratory experiments suggest that the flow of fluorine ions directly depends on the level of micro-current that is delivered, and that higher current would be beneficial for greater delivery of fluorine ions and potentially for biofilm disruption. Experiments also indicate that pulsed ionic current of 80 μA (amplitude) or less provides little oral care benefit. However, higher current levels may cause unpleasant sensations for the user, such as an electrical feeling, pain, and/or a sour taste. The embodiments described herein enable the use of higher ionic current without the associated unpleasant sensations, and may therefore provide enhanced oral care efficacy.

In some embodiments, the micro-current (I) may be ramped from a low value to a higher value each time contact is made between the brush head portion and the oral cavity of a user. In other embodiments, the amplitude of the micro-current I may remain constant. Surprisingly, the present inventors have found that higher ionic current values may be applied to the oral cavity of users without unpleasant sensations by ramping the ionic micro-current from a start current $I_{start}$ to an end current $I_{end}$ over a rise time $t_{rise}$. Generally, when the circuit is made by the application of the first electrode 106 to the oral cavity of the user, the controller circuit 104 produces a micro-current $I_{ramped}$ that starts at $I_{start}$ and increments to $I_{end}$ over $t_{rise}$, where it then is maintained at $I_{end}$ until the electrical circuit is opened by the removal of the first electrode 106 from the oral cavity of the user. Current ramping is repeated every single time the electric circuit is opened and closed. As described in more detail below, the end micro-current $I_{end}$ should be greater than about 100 μA, which is predicted to be the value of micro-current that increases brushing efficacy. In one embodiment, the end micro-current $I_{end}$ is between about 100 μA and about 800 μA. In another embodiment, the end micro-current $L_{end}$ is between about 400 μA and about 800 μA. The micro-current $I_{ramped}$ may be alternating current (AC) or direct current (DC) depending on the application. In AC applications, the micro-current ranges described above are amplitude micro-current values. It should be understood that the aforementioned micro-current ranges are intended for oral care applications, and other non-oral care applications may use different current ranges.

The time $t_{rise}$ should be long enough to minimize the sensation of the micro-current experienced by the user, but short enough such that the end micro-current $I_{end}$ is reached quickly so that the maximum current of the end micro-current $I_{end}$ is experienced by the user during the brushing session. As an example and not a limitation, the rise time $t_{rise}$ may be between 1 second and 20 seconds. Generally, the shorter the rise time $t_{rise}$, the greater the likelihood that a user will experience a sensation resulting from the micro-current. It is noted that it may be desirable for the oral care device 100 to provide some sensation to the user so that the user may be aware that a micro-current is present and the oral care device 100 is operating correctly. However, micro-currents and rise times that produce unpleasant sensations should be avoided. In one embodiment, the oral care device 100 may be programmable by the user such that the user may select variables such as rise time $t_{rise}$, start current $I_{start}$, end current $I_{end}$, a step current $I_{step}$ (the amount of increased micro-current between increments), frequency, duty cycle, etc.

FIG. 5 illustrates one exemplary AC embodiment of a micro-current ramping method. Other micro-current ramping methods may include those described and illustrated in U.S. Pat. Appl. No. 61/536,678 filed on Sep. 20, 2011, which is hereby incorporated by reference in its entirety. The operational duty cycle illustrated in FIG. 5 is 50%. Embodiments may have an operational duty cycle other than 50%, and the frequency of the pulsed ramped micro-current $I_{ramped}$ may depend on the particular application. In one embodiment, the frequency of the pulsed ramped micro-current $I_{ramped}$ is about 9 kHz.

One full micro-current pulse train 210 and one partial micro-current pulse train 220 are illustrated in FIG. 5. The micro-current starts at start micro-current $I_{start}$ when electrical contact is made between the first electrode and the oral cavity of the user (e.g., at point 211 and point 221). At first contact, the micro-current alternates between $I_{start}$ and 0 µA. The ramped micro-current $I_{ramped}$ is shifted by an offset amount $I_{step}$ such that it alternates between 0 µA and $I_{start}$ plus $I_{step}$. The micro-current shifts further by $I_{step}$ until the end micro-current $I_{end}$ is reached. The values of the ramped micro-current $I_{ramped}$ over time may be expressed as alternating between 0 and $(I_{start}+(m-1)I_{step})$ at an operational duty cycle (e.g., 50%), where m=1 upon a completion of the electrical circuit and increments by one at a step frequency until $(I_{start}+(m-1)I_{step})$. After rise time $t_{rise}$, the ramped micro-current $I_{ramped}$ then alternates between $I_{end}$ and 0 at the operational frequency until the electrical circuit is opened.

Automatic On-off Control

In some embodiments, the opening and closing of the electrical circuit that is completed by a user of an oral care device, such as an electric toothbrush, may automatically control the functionality of the oral care device. For example and referring once again to FIG. 2, the electric toothbrush 120 may be automatically operated in one operational mode, such as an OFF state or a standby state, when: 1) the user physically contacts neither the first electrode 106 in the brush head portion 129 nor the second electrode 108 on the handle portion 121, and 2) the user physically contacts only one of the first electrode 106 or the second electrode. When the user physically contacts both the first and second electrodes by gripping the second electrode 108 and placing the brush portion 129 into his or her mouth such that the first electrode 106 contacts the oral cavity, the electric toothbrush 120 may operate in another operational mode, such as one or more ON states. When the user disconnects either the first electrode 106 or the second electrode 108, or both from his or her body, the electric toothbrush 120 may switch back to the original mode (e.g., an OFF state or a standby state, as described below).

In this manner, the electric toothbrush 120 may switch between a plurality of modes based on whether or not the user has gripped the handle portion 121 and placed the brush head portion 129 into his or her mouth. In one embodiment, the electric toothbrush 120 comprises an ON-OFF switch (not shown in FIG. 2) such that when the user places the ON-OFF switch in the ON position, the electric toothbrush 120 operates in a standby state prior to the user placing the brush head portion 129 into his or her mouth (e.g., a second operational mode). During the standby state, the vibrating actuator 122 may vibrate at a low vibration amplitude and/or frequency (e.g., a non-operational vibration amplitude and/or frequency) to provide feedback to the user that the electric toothbrush 120 is working properly, without causing water and/or toothpaste to splatter from the brush head portion 129. The electric toothbrush 120 may also not produce the voltage potentials and/or waveforms associated with the micro-current delivery modes during the standby state.

When the user contacts the first electrode 106 and the second electrode 108, the controller circuit 104 may detect an impedance characteristic (e.g., resistance and/or reactance) of the electrical circuit that is completed by the user's body. In one embodiment, the controller circuit 104 compares the detected impedance characteristic with a threshold. When the detected impedance is below a threshold, or within a range associated with the impedance characteristics of the human body, the controller circuit 104 may switch to operate in one or more ON states (e.g., a first operational mode). The ON state may be any combination of operational vibration frequency, operational vibration amplitude, and micro-current delivery. The operational vibration and/or micro-current delivery may be continuously provided by the electric toothbrush 120 until a high impedance characteristic is detected by the controller circuit 104, thereby indicating disconnection of the first electrode 106 and/or the second electrode 108 from the user's body. The controller circuit 104 may then switch the electric toothbrush to the second operational mode (e.g., OFF state, standby state, or other).

In other embodiments, the electric toothbrush 120 does not include an ON-OFF switch such that the electric toothbrush 120 does not vibrate and does not produce a voltage potential at the first electrode 106 and the second electrode 108 when operating in the second operational mode (e.g., an OFF state).

In some embodiments, the controller circuit 104 further comprises a timer 141 (see FIG. 1B) that may record the operational duration of the electric toothbrush 120. The timer 141 may be configured as a distinct circuit, or be integrated into the microcontroller 112. The timer 141 may start recording time once the controller circuit 104 detects the completion of the electrical circuit via the user's body, and stop recording time once the controller detects the opening of the electrical circuit. The controller circuit 104 may record and separately store brushing duration data for individual brushing sessions in a memory component 143. The memory component may be any type of computer-readable medium, such as, but not limited to, flash memory and magnetic disk memory. Using the brushing duration data for the individual brushing sessions, the controller circuit (e.g. via the microcontroller 112) may calculate a total brushing duration for a particular oral care implement 126 that is coupled to the handle portion 121 by summing the brushing duration data for the individual brushing sessions. A user interface may be associated with the electric toothbrush 120, such as on the handle portion 121 or a separate user interface device 150 (see FIG. 7) to display brushing duration data for the individual brushing sessions and/or the total brushing duration for the particular oral care implement 126. In one embodiment, the electric toothbrush 120 may comprise an indicator, such as a light emitting diode (LED) and/or an auditory device that announces to the user when he or she has brushed long enough to meet proper brushing techniques, or that the oral care implement 126 should be replaced because the calculated total brushing duration exceeds a predetermined threshold.

The oral care implement 126 may also be designed to have a use-life that expires after a pre-determined period of use. For example, the first electrode 106 at the brush head portion 129 of an oral care implement 126 configured as a removable toothbrush head may be configured to lose electrical conductivity as a function of use. Once the first electrode 106 is no longer electrically conductive, or presents a very high impedance, the overall impedance of the electrical circuit closed by the user's body may be above the impedance threshold such that the electric toothbrush 120 will not operate in an ON state despite a user gripping the handle portion 121 and placing the brush head portion 129 in his or her mouth. Failure of the electric toothbrush 120 to turn on may indicate to the user that it is time to replace the old oral care implement with a new one.

The first electrode 106 (e.g., the first electrodes 106a-106d illustrated in FIGS. 4A-4F) may be designed to lose electrical conductivity after a predetermined period of time of predetermined brushing mode. A brushing mode may correspond to a force on which a user applies the brush head portion 129 to his or her teeth, the frequency of the brushing motion, and other factors. As an example and not a limitation, the predetermined brushing mode may correspond to a typical brushing force and brushing frequency. The first electrode 106 may be designed to wear out or otherwise lose its electrical conductivity after a predetermined period of time of average brushing, wherein the predetermined period of time corresponds with a period of time that a user should replace the oral care implement 126 due to bristle wear, for example.

The first electrode 106 may be designed to lose electrical conductivity in a variety of ways, some of which are described below. Referring once again to FIG. 4E, the first electrode is configured as an insulated conductor wire 106c. The insulated conductor wire 106c comprises an electrically conductive wire core 130 that is made out of any electrically conductive material, such as a pliable metallic material, and an outer insulator jacket 132 that surrounds the electrically conductive wire core 130. The first electrode 106 may be defined by a single insulated conductor wire 106c or a plurality of insulated conductor wires 106c. An exposed portion 130' of the electrically conductive wire core 130 may be configured to wear down or break off after a predetermined period of time of use such that the electrically conductive wire core 130 is no longer exposed to the oral cavity of the user and the first electrode 106 ceases to be electrically conductive. After the exposed portion 130' breaks off or is worn down (and as a consequence, changes its conductivity), the electronic toothbrush 120 may no longer turn on until the user replaces the oral care implement 126.

In another embodiment, the electrically conductive wire core 130 may be designed to break or otherwise fail at a predetermined breaking location 133 after the predetermined brushing duration (at a predetermined brushing mode/force) such that the portion of the electrically conductive wire core that is exposed at the end of the insulated conductor wire is not electrically coupled to the controller circuit. The predetermined breaking location 133 is covered by the outer insulator jacket 132. A break at the predetermined breaking location 133 may increase the impedance and/or prohibit the closure of the electrical circuit, thereby preventing the electric toothbrush 120 from operating in an ON state.

Referring once again to FIG. 4F, the first electrode 106 may be configured as one or more electrically conductive brush filaments 106d comprised of an electrically conductive material within a polymer (e.g., a polymer having embedded electrically conductive particles). The electrically conductive brush filaments 106d may be designed to lose conductivity over a predetermined period of time at a predetermined mode, such as a predetermined brushing force and frequency. In one embodiment, the electrically conductive particles (or film) are configured to separate from the brush filament at a loss-rate corresponding to the predetermined brushing mode. For example, the loss-rate may be such that the electrically conductive brush filament(s) 106d lose electrical conductivity after a period of time at an average brushing force and brushing frequency that corresponds with when the bristles are sufficiently worn down and the oral care implement should be replaced.

Figure 4G:
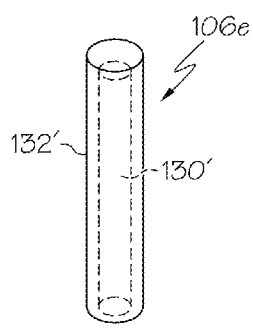

Alternatively, referring to FIG. 4G, one or more conductive filaments 106e may be provided, wherein the one or more conductive filaments 106e are configured to become conductive over time. Rather than loss of electrical conductivity or contact with the oral cavity as described above, positive electrical contact between the one or more conductive filaments 106e may indicate that the oral care implement should be replaced. The conductive filament 106e depicted in FIG. 4G has an outer insulator jacket 132' that fully surrounds an electrically conductive wire core 130'. The outer insulator jacket 132' isolates the electrically conductive wire core 130' from making electrical contact with the oral cavity of a user. However, the outer insulator jacket 132' is designed to break down over time due to brushing activity such that the electrically conductive wire core 130' is exposed. Positive electrical contact between the electrically conductive wire core 130' and the oral cavity of a user may be sensed by one or more circuits and/or controllers within the oral care device. Such electrical contact may indicate that the oral care implement should be replaced. As an example and not a limitation, sensed positive electrical contact between the electrically conductive wire core 130' and the oral cavity of the user may prevent the oral care device from operating in one or more brushing modes.

Automatic Mode Switching

In some embodiments, the oral care device, such as an electric toothbrush 120, may be configured to automatically detect which region of the oral cavity the user is brushing, and automatically switch its selected operational mode accordingly, wherein the selected operational mode is one of a plurality of operational modes. As an example and not a limitation, it may be desirable that the electric toothbrush 120 operate at a greater vibration amplitude and a greater micro-current amplitude when the user is brushing hard tissue, such as teeth, than when the user is brushing soft tissue (e.g., tongue, gums, cheeks, gingival area, etc.). Further, it may be desirable to change the vibratory motion and the micro-current amplitude/waveform depending on which tooth the user is brushing, or which particular soft tissue region the user is brushing.

Figure 6:
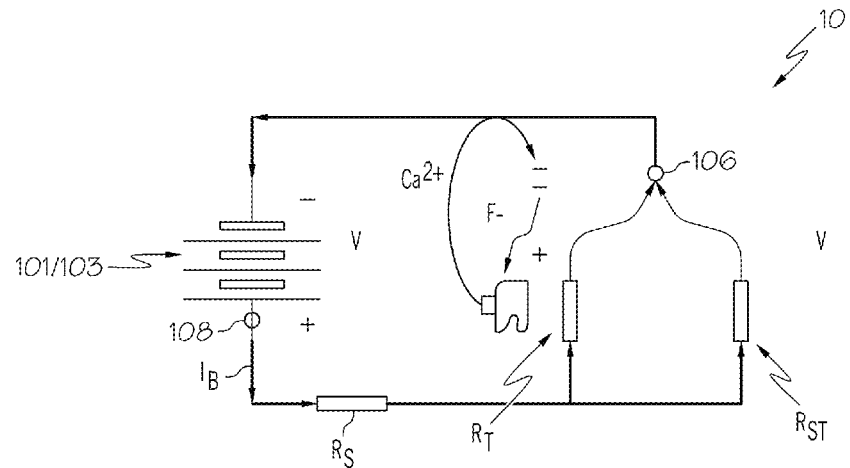
FIG. 6 schematically depicts an electrical circuit between an oral care device and a user's body according to one or more embodiments illustrated and described herein.

The electric toothbrush 120 may be configured to measure the impedance of the electric circuit and switch the operational mode depending on the measured impedance. Referring now to FIG. 6, embodiments of the present disclosure may be operable to detect the impedance of the oral cavity tissue that is in contact with the first electrode 106. The resistances of different areas within the oral cavity have characteristic value ranges. FIG. 6 depicts an electric circuit 10 defined by a power source, such as a battery and voltage regulator 101/103, a conductive path between the first electrode 106 and the power source, and a conductive path within the body of the user between the first electrode 106 and the second electrode 108 having a skin and body resistance $R_S$ and a tooth resistance $R_T$ or a soft tissue resistance $R_{ST}$. Generally, the tooth resistance is greatest: $R_T > R_{ST} > R_S$. The controller circuit 104 may calculate the overall resistance of the electric circuit 10 by measuring the ionic current $I_B$ and the voltage across the body V by R=V/I.

In one embodiment, if the measured resistance (or impedance) is more likely the resistance of a tooth, the controller circuit 104 may control the electronic toothbrush 120 (or other oral care device) to operate in a first operational mode, such as a standard mode with greater vibratory motion and greater micro-current amplitude. If the measured resistance (or impedance) is more likely the resistance of soft tissue, such as the gums or tongue, the controller circuit 104 may control the electronic tooth brush 120 (or other oral care device) in a second operational mode, such as a massage mode that has less vibratory motion and lower micro-current amplitude than the first operational mode associated with the teeth, for example. The measured resistance or impedance may be compared against stored resistance or impedance ranges to determine if the brush head portion 129 is positioned on hard or soft tissue.

Figure 7:
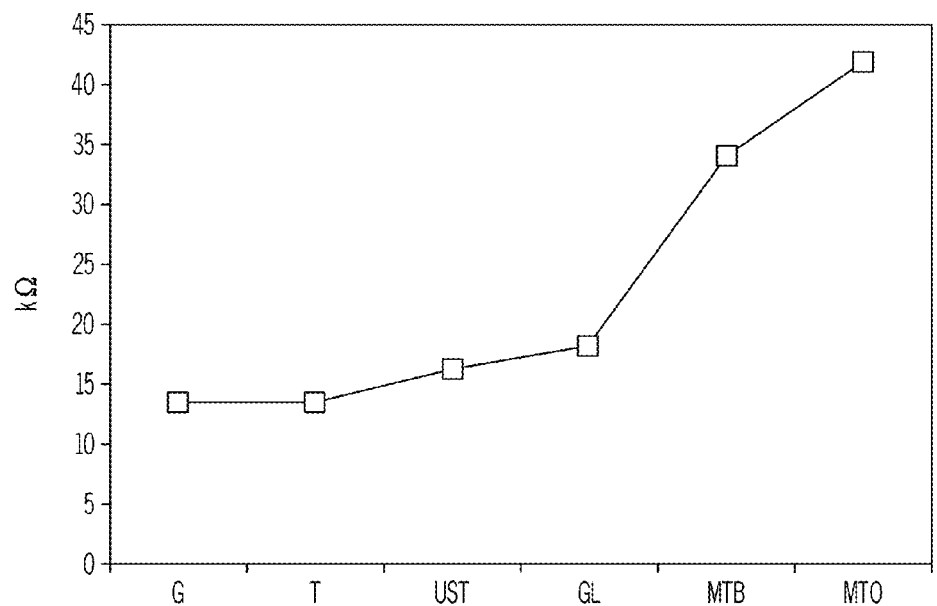
FIG. 7 graphically depicts electrical resistance of a plurality of regions within an oral cavity of a user.

Embodiments may also be configured to apply more than two different operational modes based on type of teeth and/or type of soft tissue that the first electrode 106 is in contact with. Referring now to FIG. 7, a graph depicts experimental resistance measurements of regions within the oral cavity, including a gum region G, a tongue region T, an upper jaw soft tissue region UST, a gum-tooth interface or gingival line GL, a buccal molar tooth MTB, and an occlusal molar tooth MTO. The values of the graph depicted in FIG. 7 were obtained by applying a 400 μA microcurrent I to the various regions using an electric toothbrush on a single individual. The microcurrent I was ramped at 80 μA/sec to 400 μA, and had a duty cycle of 80% and a frequency of 9 kHz. The voltage V was measured across the toothbrush head (toothbrush shaft-refill-mouth-body-toothbrush handle) using a Fluke 287 Hand Multimeter. The resistance of the various regions was calculated by R=V/I. The resistivity of the toothbrush head (shortcut measurement) was then subtracted from the measured values. Also, the 80% current duty was respected in the calculations.

As shown in the graph, the resistance of the different regions may vary such that the operational mode of the oral care device may switch depending on the type of region that is detected. The different operational modes may differ in vibratory motion (frequency and amplitude) and micro-current delivery (frequency, duty cycle, waveform shape, amplitude, etc.) to provide the greatest efficacy relating to the type of oral cavity region being brushed or massaged. In some embodiments, the type of motion may also vary between the different operational modes. As an example and not a limitation, the brush head portion may translate in three dimensions when hard tissue is detected, and only two dimensions when soft tissue is detected.

Feedback of Chemical Actives Delivery

Referring once again to FIG. 6, iontophoresis may increase the delivered amount of chemical actives that are present in an oral care substance, such as sodium fluoride toothpastes, stannous fluoride toothpastes and mouth washes, and the like. Chemical actives that may be present in the oral care substance may include, but are not limited to, $Ca^{2+}$, $F^-$, and $Sn^{2+}$. When the oral care device 120 is operated in a cathodic state such that the first electrode 106 in the brush head portion 129 has a negative polarity, anions such as $F^-$ are delivered to the teeth. When the oral care device 120 is operated in an anodic state such that the first electrode 106 in the brush head portion has a positive polarity, cations such as $Ca^{2+}$ and $Sn^{2+}$ may be delivered to the teeth.

An amount of chemical actives delivered to the teeth or soft tissue may be determined based on the amount of micro-current I that is passing through the electric circuit through the body over time t. An increase in micro-current I may lead to an increase in chemical actives delivery. Accordingly, embodiments of the present disclosure may provide feedback to the user as to the amount of chemical actives that have been delivered to the user's teeth during a brushing session via an actives delivery indicator. As an example and not a limitation, the delivered amount may be shown using LEDs 160 on the handle portion 121 of the electric toothbrush 120 starts red, then turns yellow and then green over time t as the user brushes his or her teeth. Any number of LEDs may be provided. Each LED may be associated with a particular actives delivery range. As another example and not a limitation, the electric toothbrush may have a gauge-like display that graphically depicts the amount of chemical actives that have been delivered over time t. The amount of chemical actives that is delivered may be recorded by the controller circuit 104 and stored in a memory component 143 for later use, such as statistical analysis.

Figure 8:
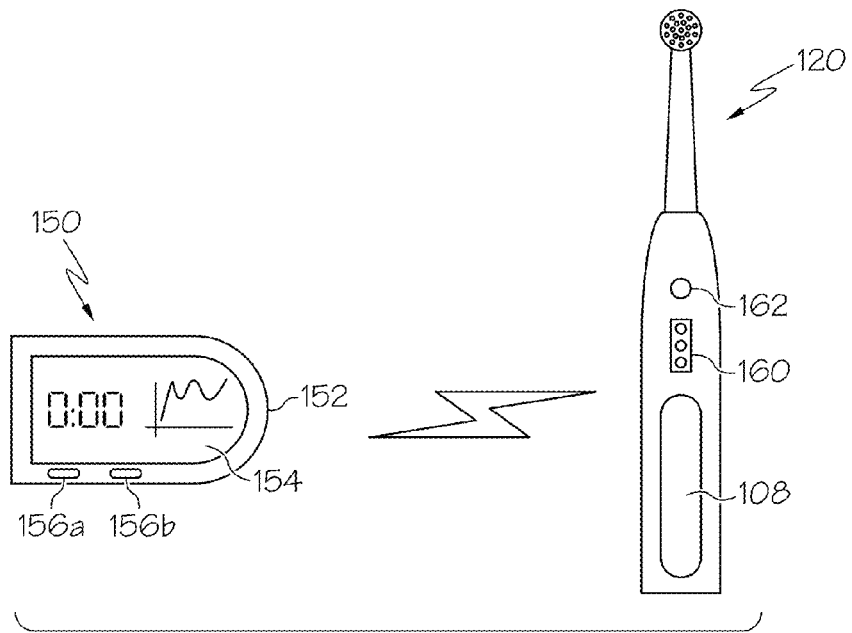
FIG. 8 schematically depicts an oral care device in wireless communication with a user interface device according to one or more embodiments illustrated and described herein.

Referring now to FIG. 8, an electric toothbrush 120 is schematically depicted in wireless communication with an actives delivery indicator configured as a separate user interface device 150 comprising a housing 152 and a graphical display 154. The electric toothbrush 120 may transmit a wireless signal from the wireless communications module 140 to the actives delivery indicator for a graphical representation of the amount of chemical actives delivered to the oral cavity on the graphical display 154. The user interface may include an alphabetic display, a numeric display, an alpha-numeric display, or combinations thereof. The user interface device 150 may also comprise one or more input hard keys 156a, 156b. In one embodiment, the amount of chemical actives delivered during past brushing sessions may be stored in the user interface device 150 for later retrieval and display on the graphical display 154.

In some embodiments, the controller circuit 104 (e.g., the microcontroller 112 of the controller circuit 104) may be configured to receive a code associated with the particular oral care substance being used for the particular brushing session. For example, the packaging of the oral care substance, such as a tube of toothpaste, may have a code that may be entered into the electric toothbrush 120 or the user interface device 150 by the user (e.g., manually or automatically by a scanner or another input device that is a component of the electric toothbrush 120 or the user interface device 150 or a separate input device). As another example, the code may be configured as a bar code or an image that may be recognized by a camera within a computing device such as a smartphone, an electric toothbrush 120, or a user interface device 150 by image recognition techniques. The code may then be interpreted by the microcontroller 112 such that the microcontroller is aware of the type oral care substance and the percentage of chemical actives that are present in such a type of oral care substance. Using this information, the controller circuit 104 may calculate the amount and type of chemical actives that are delivered based on the amount of micro-current I and the time t.

Hard Tissue Diagnosis

In some embodiments, the oral care device, such as an electric toothbrush 120, may be configured to diagnose the health status of a user's teeth over using electrical impedance spectroscopy. Embodiments of the present disclosure may measure the system impedance of the user's tooth or teeth over a range of frequencies. It has been shown that caries lesions in teeth affect the electrical impedance of the teeth, which may be due to loss of enamel. Teeth containing a cavity may have a lower electrical resistance than healthy teeth.

Referring again to FIG. 3, the controller circuit 104 may produce a substantially sinusoidal micro-current I across a range of frequencies after completion of the electrical circuit between the first electrode 106 and the second electrode 108 to diagnose the health status of a tooth. The user may place the brush head portion 129 of the oral care implement 126 on a single tooth that he or she desires to diagnose. The substantially sinusoidal micro-current I may pass through the tooth across the range frequencies. The controller circuit 104 comprises a frequency analyzer circuit 142 that is configured to detect a system impedance of the tooth across using the substantially sinusoidal micro-current I. In one embodiment, the frequency analyzer circuit 142 is a distinct circuit (or integrated circuit) within the controller circuit 104. In another embodiment, the functionality of the frequency analyzer circuit is provided by the microcontroller 112. Any frequency analyzer circuit capable of determining the spectral content of a response of the tooth may be utilized.

The controller circuit 104, via the microcontroller 112 or a separate frequency analyzer circuit 142, may measure a fundamental-harmonic component of a response of the substantially sinusoidal micro-current I through the electric circuit, including the tooth being diagnosed. The controller circuit 104 may then calculate or otherwise determine the system impedance from the fundamental-harmonic component of the response, which may include the real and/or imaginary parts of the system impedance.

In one embodiment, the system impedance of the tooth under diagnosis is compared with a plurality of impedance values that correspond to health statuses (e.g., healthy tooth, some decay, significant decay, etc.). The microcontroller 112 may select the impedance value that is closest to the system impedance and store it and/or the health status associated with the selected impedance value in the memory component 143 for later use and retrieval. The above-described process may be performed for each tooth such that each tooth may be diagnosed.

Additionally, embodiments may track the health status of individual teeth over time. In one embodiment the user may record the health status of his or her teeth by diagnosing each tooth according to a sequence. During each diagnosis session, the user will diagnosis his or her teeth in a particular sequence such that the health status and/or system impedance value for each tooth are stored in a table or other format for comparison over time. The health status data of the table may be graphically presented to the user so that the user may track the health status of his or her teeth. The current and past health status data may be compared against future system impedance values and health statuses.

The data may be transmitted and stored in the user interface device 150 (see FIG. 8) for graphical presentation. Further, the health status data may be transmitted to the user's dentist or other health care provider for teeth diagnosis monitoring over time. As an example and not a limitation, the health status of the right maxillary canine may be recorded and tracked over time for evaluation by the user and/or the user's dentist.

Automatic Oral Care Implement Detection and Mode Switching

Referring generally to FIG. 2, some embodiments of the oral care device, such as an electric toothbrush 120, may be configured to detect the type of oral care implement 126 that is coupled to the handle portion 121. The controller circuit 104 may then control the operation of the electric toothbrush 120 depending on the detected type of oral care implement 126. For example, if the controller circuit 104 cannot determine the type of oral care implement because the oral care implement does not possess particular characteristics, the controller circuit 104 may not allow vibrating actuator 122 to vibrate and/or the micro-current I to be provided. In this manner, the controller circuit 104 may be able to detect the type of oral care implement and control the electric toothbrush 120 accordingly. In one embodiment, the electric toothbrush or a separate user interface device (e.g., the user interface device 150 depicted in FIG. 8) may provide an indication that the oral care implement is not compatible with the electric toothbrush when the impedance is not within any predetermined impedance range. In one embodiment, a visual indication may be provided by one or more LEDs associated with the electric toothbrush.

Figure 9:
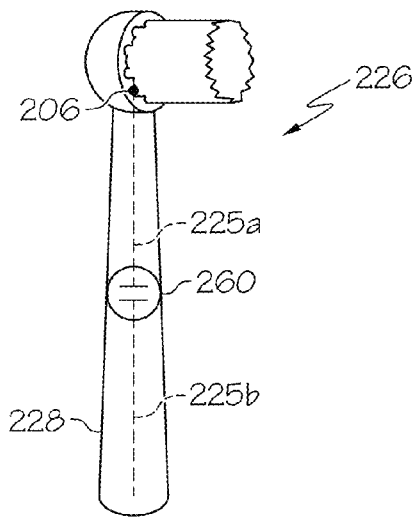
FIG. 9 schematically depicts an oral care implement according to one or more embodiments illustrated and described herein.

Referring now to FIG. 9, an oral care implement 226 according to one embodiment is schematically illustrated. In the illustrated embodiment, an impedance element 260 is provided within the oral care implement 226 such that impedance element 260 is within an electrically conductive path (indicated by dashed lines 225a, 225b) and electrically coupled to the first electrode 206 and a handle portion (not shown in FIG. 9) when the oral care implement 226 is physically coupled to the handle portion of an electric toothbrush. The illustrated impedance element 260 is depicted as a capacitive element. The impedance element 260 may also be configured as a resistive element or an inductive element. In another embodiment, the impedance element 260 may comprise a circuit made up of a combination of one or more capacitive elements, resistive elements, and inductive elements. The impedance characteristic of the impedance element 260 may correspond to the type of oral care implement that may affect the mode of toothbrush operation. For example, an impedance element 260 having an impedance characteristic within a first impedance range may correspond to a "regular" toothbrush head, while an impedance element 260 having an impedance characteristic within a second impedance range may correspond to a "sensitive" toothbrush head. A "regular" toothbrush head may have a greater vibratory motion (e.g., vibration frequency and/or vibration amplitude) and/or increased micro-current amplitude than the "sensitive" toothbrush head.

Referring to FIGS. 2, 3 and 9, the controller circuit 104 may be configured to detect the impedance of the oral care implement 226 that is coupled to the handle portion 121. The impedance of the oral care implement 226 is affected by the impedance element 260, which in the illustrated example is capacitance. In one embodiment, the controller circuit generates a micro-current I through the user between the first electrode and the second electrode at a first micro-current amplitude (or frequency, duty cycle, waveform shape, etc.) when the impedance characteristic is within a first impedance range, and at a second micro-current amplitude (or frequency, duty cycle, waveform shape, etc.) when the predetermined impedance characteristic is within a second impedance range. In this manner, the amplitude of the micro-current I may be adjusted depending on the type of oral care implement 226 that is detected. It should be understood that the controller circuit 104 may generate the micro-current I through the user at additional micro-current amplitudes when the impedance is within one or more additional impedance ranges.

The type of oral care implement may also affect the vibratory motion of the oral care implement as controlled by the control circuit 104. The controller circuit 104 may provide a first signal to the vibrating actuator 122 when the impedance is within the first impedance range such that the vibrating actuator 122 vibrates at a first vibration frequency and/or a first vibration amplitude. Similarly, the controller circuit 104 may provide a second signal to the vibrating actuator when the impedance is within the second impedance range such that the vibrating actuator 122 vibrates at a second vibration frequency and/or second vibration amplitude. Additional vibration modes corresponding to additional impedance ranges may be provided.

It should be understood that some operational modes may provide for application of micro-current I only, while other operational modes may provide for vibratory motion of the oral care implement 226 only. Yet other operational modes may provide for various combinations of micro-current I application and vibratory motion of the oral care implement 226.

Referring now to FIGS. 10 and 10A, an electric toothbrush 320 capable of automatically detecting a type of oral care implement 326 by electric resonant frequency detection (or electric anti-resonant frequency, in alternative embodiments) is schematically illustrated. In this embodiment, each type of oral care implement 326 (e.g., "regular" toothbrush head, "sensitive" toothbrush head, tongue massager, and the like) has a predefined electric resonant frequency. The controller circuit 104 may be configured to probe the oral care implement 326 to determine if it is an authorized oral care implement and, if so, the type of oral care implement. The controller circuit 104 may control the electric toothbrush 320 according to an operational mode corresponding to the type of oral care implement 326 that is detected.

Different oral care implements 326 may be designed with different electric resonance frequencies. The different oral care implements 326 may be recognized and the appropriate maximum micro-current amplitudes (and/or vibratory motion of the brush head portion) can be applied to achieve an optimal cleaning result. In one embodiment, the electric resonant frequency of the oral care implement 326 is established by an electro-active polymer within the oral care implement 326. For example, an electro-active polymer 370, such as a piezoelectric active polymer, may be provided within at least a portion of a stem 328 of the oral care implement 326. The electro-active polymer 370 within the oral care implement 326 is designed such that the oral care implement 326 has an electric resonant frequency (or an electric anti-resonant frequency) within a predetermined frequency range.

FIG. 10A depicts an equivalent analog circuit 380 of the electro-active polymer 370, which has resistive, inductive and capacitive properties. To determine the electric resonant or anti-resonant frequency of the oral care implement 326, the controller circuit 104 (see FIG. 3) generates an evaluation micro-current $I_{eval}$ through the electrical circuit closed by the user's body B. The evaluation micro-current $I_{eval}$ is swept across an evaluation frequency range. As an example and not a limitation, the electro-active polymer is chosen such that its impact on the impedance of the oral care implement 326 is above 10 MHz. Accordingly, the evaluation frequency range should be proximate 10 MHz in this example. It is noted that the tooth/body impact on impedance is in the range below 1 MHz. Accordingly, the resonant peaks of the electro-active polymer circuit should be in a frequency range that is not influenced by human body impedance.

The controller circuit 104 detects the impedance Z of the electrical circuit as the evaluation micro-current $I_{eval}$ is swept across the evaluation frequency range. FIG. 11 depicts exemplary impedance response of two exemplary piezoelectric polymer oral care implements 326 as a function of frequency f. Curve $Ref_1$ corresponds to a first oral care implement refill, and curve $Ref_2$ corresponds to a second oral care implement refill. "Refill" means a replacement oral care implement. As shown in FIG. 11, the first oral care implement refill has an electric resonant frequency $f_{R1}$ and an electric anti-resonant frequency $f_{AR1}$. The second oral care implement refill has an electric resonant frequency $f_{R2}$ and an electric anti-resonant frequency $f_{AR2}$. The electric resonant and anti-resonant frequencies of the first oral care implement refill are less than the electric resonant and anti-resonant frequencies of the second oral care implement refill. Because the electric resonant and anti-resonant frequencies are different, the type of oral care implement may be detected.

The controller circuit 104 may compare the electric resonant frequency or the anti-resonant frequency with a plurality of frequency ranges. If the electric resonant frequency or the anti-resonant frequency is within one of the plurality of frequency ranges, the controller circuit 104 may generate a micro-current I (and/or provide a particular vibratory motion) through the user in accordance with the type of oral care implement 326 associated with that particular frequency range. For example, the controller circuit 104 may generate a micro-current I through the user between the first electrode and the second electrode at a first micro-current amplitude when the detected resonant electrical frequency is within a first frequency range, and at a second micro-current amplitude when the detected resonant electrical frequency is within a second frequency range. Additional micro-current amplitude ranges (as well as other micro-current properties, such as duty cycle, frequency, etc.) corresponding to additional operational modes may also be provided.

It should now be understood that embodiments described herein enable increased ionic micro-current levels in iontophoresis applications without imparting unpleasant sensations in the user or patient by ramping the micro-current from a start current to an end current over a rise time. In oral care applications, the ramped micro-current reduces the voltage drop in the oral cavity, and allows for current levels of greater than 100 µA. The ramping of micro-current techniques described herein may be implemented in any number of iontophoresis applications.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be understood to those skilled in the art that various other changes and modifications can be made without departing from the spirit and scope of the invention. It is therefore intended to cover in the appended claims all such changes and modifications that are within the scope of this invention.

What is claimed is:
1. An oral care device comprising:
   a handle portion;

an oral care implement coupled to the handle portion, the oral care implement comprising a brush head portion comprising brush filaments;

a first electrode located in the brush head portion and operable to be in electrical contact with an oral cavity of the user;

a second electrode located in the handle portion and operable to be in electrical contact with a hand of a user;

a power source providing a voltage potential between the first electrode and the second electrode;

a controller circuit electrically coupled to the first electrode, the second electrode, and the power source, electrical contact of the second electrode at the hand of the user and electrical contact of the first electrode at the oral cavity of the user completes an electrical circuit between the first electrode and the second electrode;

the first electrode electrically decoupled from the controller circuit and the power source after a predetermined operational duration of the oral care device;

the controller circuit detects a completion or an opening of the electrical circuit by measuring an impedance through the user between the hand of the user and the oral cavity of the user, such that a measured impedance above a threshold indicates the opening of the electrical circuit and a measured impedance below the threshold indicates the completion of the electrical circuit;

upon detection of the completion of the electrical circuit, the controller circuit controls the oral care device to operate at a first operational mode; and upon detection of the opening of the electrical circuit, the controller circuit controls the oral care device to operate at a second operational mode wherein the first electrode includes one or more conductive brush filaments positioned proximate to the brush filaments, the one or more conductive brush filaments including an electrically conductive material within a polymer; and further wherein electrically conductive carbon particles separate from the one or more conductive brush filaments at a loss-rate corresponding to a predetermined brushing mode.

2. The oral care device of claim 1, wherein:

upon detection of the completion of the electrical circuit, the controller circuit controls the oral care device to operate in the first operational mode by generating a micro-current I through the user between the first electrode and the second electrode; and upon detection of the opening of the electrical circuit, the controller circuit controls the oral care device to operate in the second operational mode by stopping the micro-current I through the user between the first electrode and the second electrode.

3. The oral care device as claimed in claim 1, wherein the controller circuit records a brushing duration by initiating a timer when the controller circuit detects the completion of the electrical circuit, and stopping the timer when the controller circuit detects the opening of the electrical circuit.

4. The oral care device as claimed in claim 3, wherein the controller circuit records the brushing duration for multiple, independent brushing sessions.

5. The oral care device as claimed in claim 4, wherein the controller circuit records a total brushing duration for the brush head portion.

6. The oral care device as claimed in claim 1, wherein separation of the electrically conductive carbon particles causes the one or more conductive brush filaments to lose electrical conductivity over time.

7. The oral care device as claimed in claim 1, wherein the first electrode comprises an insulated conductor wire, the insulated conductor wire comprising an electrically conductive wire core and an outer insulator jacket surrounding the electrically conductive wire core such that a portion of the electrically conductive wire core is exposed at an end of the insulated conductor wire.

8. The oral care device as claimed in claim 7, wherein the insulated conductor wire stops being electrically conductive after a predetermined brushing duration at a predetermined brushing mode.

9. The oral care device as claimed in claim 8, wherein the portion of the electrically conductive wire core that is exposed at the end of the insulated conductor wire breaks off after the predetermined brushing duration at the predetermined brushing mode.

10. The oral care device as claimed in claim 8, wherein the electrically conductive wire core breaks at a predetermined breaking location that is covered by the outer insulator jacket after the predetermined brushing duration at the predetermined brushing mode such that the portion of the electrically conductive wire core that is exposed at the end of the insulated conductor wire is not electrically coupled to the controller circuit.

11. The oral care device as claimed in claim 1, wherein the first electrode is defined by a plurality of conductive brush filaments that are electrically coupled to the controller circuit.

12. The oral care device as claimed in claim 11, wherein individual conductive brush filaments of the plurality of conductive brush filaments cease being electrically conductive after a predetermined brushing duration and a predetermined brushing mode such that the impedance measured by the controller circuit when the brush head portion is positioned in the oral cavity of the user increases over time.

13. The oral care device as claimed in claim 1, further comprising a vibrating actuator operable to vibrate at a vibration amplitude and frequency to translate the brush head portion at the vibration amplitude and frequency.

14. The oral care device of claim 13, wherein:

upon detection of the completion of the electrical circuit, the controller circuit controls the oral care device to operate in the first operational mode by generating a micro-current I through the user between the first electrode and the second electrode, and controlling the vibrating actuator to vibrate at the operational vibration amplitude and frequency; and upon detection of the opening of the electrical circuit, the controller circuit controls the oral care device to operate in the second operational mode by stopping the micro-current I through the user between the first electrode and the second electrode, and controlling the vibrating actuator to stop vibrating at the operational vibration amplitude and frequency.

15. The oral care device of claim 14, wherein the vibration actuator vibrates at a non-operational vibration amplitude and frequency that is less than the operational vibration amplitude and frequency, respectively, when the oral care device operates in the second operational mode.

16. An oral care device comprising:

a handle portion;

an oral care implement coupled to the handle portion, the oral care implement comprising a brush head portion comprising brush filaments;

a first electrode located in the brush head portion and operable to be in electrical contact with an oral cavity of the user;

a second electrode located in the handle portion and operable to be in electrical contact with a hand of a user;

a power source providing a voltage potential between the first electrode and the second electrode;

a vibrating actuator operable to vibrate at a vibration amplitude and frequency to translate the brush head portion at the vibration amplitude and frequency; and a controller circuit in electrical communication with the vibrating actuator, the first electrode, the second electrode, and the power source, electrical contact of the second electrode at the hand of the user and electrical contact of the first electrode at the oral cavity of the user completes an electrical circuit between the first electrode and the second electrode;

the controller circuit detects a completion or an opening of the electrical circuit by measuring an impedance through the user between the hand of the user and the oral cavity of the user, such that a measured impedance above a threshold indicates the opening of the electrical circuit and a measured impedance below the threshold indicates the completion of the electrical circuit;

upon detection of the completion of the electrical circuit, the controller circuit controls the oral care device to operate in the first operational mode by generating a micro-current I through the user between the first electrode and the second electrode, and controlling the vibrating actuator to vibrate at the operational vibration amplitude and frequency; and upon detection of the opening of the electrical circuit, the controller circuit controls the oral care device to operate in the second operational mode by stopping the micro-current I through the user between the first electrode and the second electrode, and controlling the vibrating actuator to stop vibrating at the operational vibration amplitude and frequency.

\* \* \* \* \*